United States Patent [19]
Elkhoury

[11] Patent Number: 6,143,278
[45] Date of Patent: Nov. 7, 2000

[54] TOPICAL APPLICATION OF OPIOID ANALGESIC DRUGS SUCH AS MORPHINE

[76] Inventor: George F. Elkhoury, 1561 Ramillo Ave., Long Beach, Calif. 90815

[21] Appl. No.: 09/028,117

[22] Filed: Feb. 23, 1998

[51] Int. Cl.$^7$ ............................... A61K 9/12; A61K 9/06; A61K 31/485
[52] U.S. Cl. ........................... 424/45; 424/484; 424/485; 424/486; 424/487; 424/488; 424/43; 514/282; 514/812; 514/944; 514/946; 514/947; 514/969
[58] Field of Search .................................... 424/484–488, 424/43, 45; 514/810, 812, 944, 969, 278, 279, 281, 282, 946, 947, 788

[56] References Cited

U.S. PATENT DOCUMENTS

| | | | |
|---|---|---|---|
| 3,275,510 | 9/1966 | Magid et al. | 514/946 |
| 4,416,886 | 11/1983 | Bernstein | 424/260 |
| 4,626,539 | 12/1986 | Aungst et al. | 514/282 |
| 4,783,450 | 11/1988 | Fawzi et al. | 514/78 |
| 4,871,750 | 10/1989 | Roberts | 514/328 |
| 4,897,260 | 1/1990 | Ross et al. | 424/59 |
| 5,069,909 | 12/1991 | Sharma et al. | 424/499 |
| 5,503,844 | 4/1996 | Kwiatek et al. | 424/449 |
| 5,589,480 | 12/1996 | Elkhoury et al. | 514/282 |

FOREIGN PATENT DOCUMENTS

WO 9213540  8/1992  WIPO.

OTHER PUBLICATIONS

J. L. Joris et al., *Anesth. Analg.*, Opioid Analgesia At Peripheral Sites: A Target for Opioids Released During Stress and Inflammation? 66:1277–81 (1987).

H. Bouaziz, MD et al., *Anesth Analg.*, "Postoperative Analgesia from Intrathecal Neostigmine in Sheep," 80:1140–4 (1995).

G. Lauretti, MD et al., *Anesth Analg.*, "Dose–Response Study of Introthecal Morphine Versus Intrathecal Neostigmine, Their Combination . . . " 82:1182–7 (1996).

S. Abram, MD et al., *Anesth Analg.*, "Intrathecal Acetyl Cholinesterase Inhibitors Produce Analgesia That is Synergistic with Morphine and Clonidine in Rats," 81:501–7 (1995).

C. Stein, M.D. et al., *New England Journal of Medicine,* vol. 325, No. 16 "Analgesic Effect of Intraarticular Morphine After Arthroscopic Knee Surgery," pp. 1123–1126.

T. Yaksh, Ph.D. et al., *Anesthesiology,* "Studies on the Safety of Chronically Administered Intrathecal Neostigmine Methylsulfate in Rats and Dogs," V 82. No. 2, Feb. 1995.

"Morphine—A 'Local Analgesic,'" International Association for the Study of Pain, vol. III.

G. Lauretti, MD et al., *Anesth Analg* "The Effects of Intrathecal Neostigmine on Somatic and Visceral Pain: Improvement by Associate with a Peripheral Anticholinergic," 81:615–20 (1996).

D. Hood, M.D., et al., *Anesthesiology,* "Phase I Safety Assessment of Intrathecal Neostigmine Methylsulfate in Humans," V 82., No. 2, Feb. 1995 pp. 331–342.

Goodman & Gillman's, *The Pharmacological Basis of Therapeutics,* 9th Ed., McGraw–Hill pp 141–175.

Tennant et al. Abs. of Int. Pharm. Abs. (Lancet) v. 342 (Oct. 23, 1993) p. 1047–1048.

Letters to the Editor, *The Lancet,* vol. 342, Oct. 23, 1993, pp. 1047–1048.

C. Stein, M.D., "The Control of Pain in peripheral Tissue by Opioids," *Mechanisms of Disease,* vol. 332, No. 25, pp. 1685–1690, (1995).

C. Williams, Intrasite Gel: A Hyrogel Dressing, Product Focus (3–page article).

Remington Pharmaceutical Sciences 18th ed., Chapter 87, "Medicated Applications," pp. 1596–1614 (1990).

C. Stein, "Peripheral and Non–Neuronal Opioid Effects," *Current Scient Ltd.,* 1–85922–136–X ISSN 0952–7907, pp. 347–351.

S. Moiniche, et al., "Peripheral Antinociceptive Effects of Morphine After Burn Injury," *Acta Anaesthesiologica Scandinavica,* ISSN 0001–51772, pp. 710–712 (1993).

C. Stein, "Peripheral Mechanisms of Opioid Analgesia," *Anesth Analg* 1993; 76:182–92.

C. Stein et al., "Peripheral Opioid Receptors," *Annals of Medicine* 17:219–221 (1995).

*Primary Examiner*—Neil S. Levy
*Attorney, Agent, or Firm*—Millen, White, Zelane & Branigan, P.C.

[57] ABSTRACT

The invention is directed to methods and pharmaceutical compositions for the topical administration of opioid analgesic drugs such as morphine. In particular, the invention relates to topical administration of an opioid analgesic agent, e.g., morphine sulfate, in admixture with a skin- or mucosal-specific penetration enhancer, to produce a localized analgesic effect in inflamed or non-inflamed skin or mucosal tissue, and without a transdermal or transmucosal migration of opioid agent, e.g., into the systemic circulation.

6 Claims, 1 Drawing Sheet

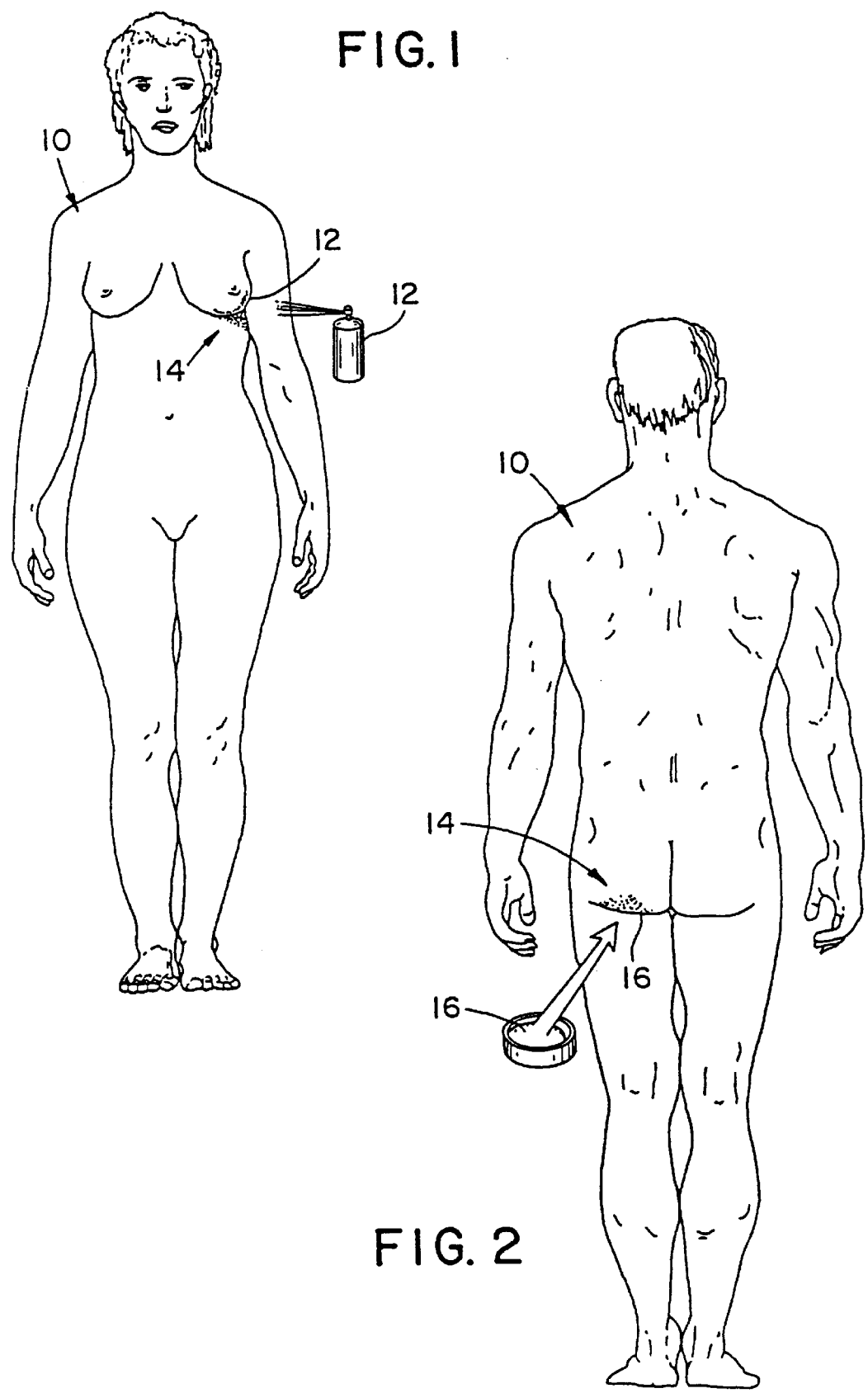

TOPICAL APPLICATION OF OPIOID ANALGESIC DRUGS SUCH AS MORPHINE

BACKGROUND OF THE INVENTION

Morphine is the prototype of the class of opioid analgesic drugs which exert their effects by activating opioid receptors within the brain. When morphine is referred to individually in this application, this reference is meant to encompass other opioid drugs and is not meant to be morphine exclusively. Historically, narcotics have been used since the 18th century in the forms of oral or injectable morphine or opium in order to accomplish pain relief. Morphine is considered to be unsurpassed as an analgesic for severe pain.

Unfortunately, morphine and other opioid drugs have a number of severe side effects which hamper their wide spread use and acceptance by both physicians and patients. These side effects include: addiction, nausea, inhibition of breathing, somnolence and dysphoria, all of which are mediated by morphine's action within the brain. It is still the current belief that narcotics ingested or injected will cross to the blood stream and from there go to the brain where there are morphine receptors. At that time, the narcotics are believed to attach to these morphine receptors and create a dullness of the pain but with all of the side effects described above. Of course, the worst potential effect is the addiction that can occur if the morphine is used beyond a few days or weeks on a continuous basis.

Because of the fear of addiction, the use of morphine as an analgesic has been restricted. In addition, major research efforts have been directed toward the development of morphine-like drugs that act within the brain but are devoid of the side effects. The market for these other drugs has never fully materialized because these drugs were not perceived as having the same analgesic properties of morphine and because typically these drugs were not produced to be both available in oral and injectable formats.

In the past ten years, the intraspinal method of treating pain has been extensively developed but, as more extensive use was made of this technique, a number of serious problems developed. The first problem is that the intraspinal method of treatment requires a spinal tap which of course necessitates the use of a needle to the spinal cord. The second problem results from the first in that if it is necessary to use the intraspinal method over a period of time, such as two or three weeks, medication must be injected into the spine for this period of time and the continuous needle sticks into the spine has potential hazards. Further, if it is necessary to use the intraspinal method over time, even though the dosage is substantially less compared to oral or intravenous dosages, there is still a high potential for addiction and with such addiction the resultant problems of withdrawal and its associated side effects.

Although intraspinal application of narcotics is still used to alleviate pain after surgery, this technique has the limitations with the potential for addiction as described above. In addition, it has been determined that with frail patients there is the risk that the patient can stop breathing and there have been a number of cases of respiratory arrest after the administration of narcotics using the intraspinal technique. Further, the intraspinal technique of administering narcotics creates difficulty with male patients and especially with elderly male patients in that there can be problems with urination and with consequent problems of urine retention. Finally, this intraspinal technique produces a significant itching problem as a side effect.

In more recent studies it was discovered that opioid receptors may also be located in other peripheral tissues. This was reported in Stein, C. et al., Peripheral effect of fentanyl upon nociception in inflamed tissue of the rat. Neurosci. Lett. 84:225–228 (1988), and in Stein, C. et al., Antinociceptive effects of mu- and kappa-agonists in inflammation are enhanced by a peripheral opioid receptor-specific mechanism of action. Eur. J. Pharmacol. 155:255–264 (1988). Subsequently, animal experiments were performed in Dr. Stein's laboratory characterizing peripheral opioid receptors and their activation by morphine and other opioid drugs. This was reviewed in Stein, C., Peripheral mechanisms of opioid analgesia. Anesth. Analg. 76:182–191 (1993), and in Stein, C., Lehrgerger, K., Yassouridis, A., Khoury, G.: Opioids as novel intraarticular agents in arthritis. In: Progress in Pain Research and Management, Fields, H. L., Liebeskind, J. C., eds., 1:289–296, IASP Press, Seattle, (1994). A most important determination from these various studies is that the doses of the drugs required to produce analgesia in the peripheral tissues are extremely small and therefore devoid of the above mentioned side effects produced by dosages sufficient to operate on the brain.

In addition, it was determined that the endogenous ligands of peripheral opioid receptors (endorphins, the body's own pain killers) are located within the inflamed tissue. It was also determined that the endorphins can produce intrinsic analgesia within peripheral tissues both in animals and in humans (Stein (1993), ibid.). It was further noted that the peripheral opioid effects were more pronounced in inflamed than in non-inflamed tissues.

An anecdotal preliminary study reported an attempt to transdermally locally administer 1–3 mg of morphine to the backs of patients who had undergone failed back operations, primarily using mechanical methods of enhancing skin penetration and absorption of the morphine (ultrasound, massage, heat) as well as by the use of the occlusive topical vehicle Aquaphor (F. Tennant et al., Topical morphine for peripheral pain. Lancet 342:1047–1048 (1993)). Some improvement in pain relief was noted, and the authors speculated that it was due to binding of the morphine to peripheral opioid receptors in inflamed (presumably myofascial) tissue directly under the skin to which the morphine was applied, and absence of morphine in the systemic circulation was claimed. This result is scientifically questionable, however, based on the data of the present invention: there had to be sufficient transdermal transport to carry the morphine completely through the skin and into the underlying inflamed myofascial tissues, which would almost certainly result in a detectable amount of morphine being carried in the systemic circulation. Alternatively, it is possible that the pain relief noted was not reproducible. It is notable that no further reports of this type of administration have been reported since, either by that group or any others.

None of these reports discussed the possibility that pain relief could be topically induced in skin, whether inflamed or not, nor was it even known whether peripheral opioid receptors are present in human skin.

Severe pain caused or accompanied by inflammation in skin is a particularly intractable problem, because the underlying reasons for it tend to be both long-term and yet not inherently life-threatening, e.g., shingles and various kinds of burns, both of militate against the chronic systemic use of opioid agents. This led to initial investigations into whether it might be possible to be able to induce effective opioid analgesia in such cases without the negative effects of systemic opioid administration. U.S. Pat. No. 5,589,480, ElKhoury and Stein, discloses the use of topical opioid analgesics in inflamed skin or mucosal tissue, whereby effective analgesia in the inflamed skin or mucosal tissue is induced in the substantial absence of transdermal or transmucosal delivery of the opioid analgesic agent. As with any such application, improvements in the effectiveness of the methods and preparations, e.g., in the effectiveness of analgesia thus induced, would be desirable.

However, as noted above, peripheral opioid effects are more pronounced in inflamed than in non-inflamed tissues. There still remains the problem of severe pain in intact skin unaccompanied by inflammation, which also is an intractable problem, again, because the underlying reasons for it tend to be both long-term and yet not inherently life-threatening, e.g., diabetic peripheral neuropathy and postherpetic neuralgia, both of which militate against the chronic systemic use of opioid agents. Therefore, it would be a great benefit to be able to induce effective opioid analgesia in such cases without the negative effects of systemic opioid administration.

SUMMARY OF THE INVENTION

This invention provides a method of inducing analgesia in intact, non-inflamed skin or mucosal tissue, comprising topically administering to a patient in need of such treatment a topically effective amount of an opioid analgesic agent, which amount is systemically ineffective for induction of analgesia, admixed with a skin- or mucosa-specific penetration enhancer, such as, e.g., lecithin, and a pharmaceutically acceptable excipient for topical administration, preferably whereby effective analgesia in the non-inflamed skin or mucosal tissue is induced in the substantial absence of transdermal or transmucosal delivery of the opioid analgesic agent to the systemic circulation.

The invention further provides a method of inducing analgesia in inflamed skin or mucosal tissue, comprising topically administering to a patient in need of such treatment a topically effective amount of an opioid analgesic agent, which amount is systemically ineffective for induction of analgesia, admixed with a skin- or mucosa-specific penetration enhancer, such as, e.g., lecithin, and a pharmaceutically acceptable excipient for topical administration, whereby effective analgesia in the inflamed skin or mucosal tissue is induced in the substantial absence of transdermal or transmucosal delivery of the opioid analgesic agent to the systemic circulation.

A further object of the invention is to provide a pharmaceutical composition comprising an admixture of an opioid analgesic agent, a skin- or mucosa-specific penetration enhancer, such as, e.g., lecithin, and a pharmaceutically acceptable excipient for topical administration to non-inflamed skin or mucosal tissue, wherein a unit dosage amount of the admixture contains a systemically ineffective amount of the opioid analgesic agent and an effective amount of a skin-specific penetration enhancer, such as, e.g., lecithin, and neither the skin-specific penetration enhancer nor the excipient substantially enhances transdermal or transmucosal transmission of the opioid analgesic agent into the systemic circulation, with the proviso that, when the admixture is a liquid, it further comprises a component that is pharmaceutically unacceptable for parenteral administration.

A still further object of the invention is to provide a pharmaceutical composition comprising an admixture of an opioid analgesic agent, a skin-specific penetration enhancer, such as, e.g., lecithin, and a pharmaceutically acceptable excipient for topical administration to inflamed skin or mucosal tissue, wherein a unit dosage amount of the admixture contains a systemically ineffective amount of the opioid analgesic agent and an effective amount of a skin- or mucosa-specific penetration enhancer, such as, e.g., lecithin, and neither the skin- or mucosa-specific penetration enhancer nor the excipient substantially enhances transdermal or transmucosal transmission of the opioid analgesic agent into the systemic circulation, with the proviso that, when the admixture is a liquid, it further comprises a component that is pharmaceutically unacceptable for parenteral administration.

Upon further study of the specification and claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 illustrates a method and apparatus of the present invention and specifically shows a patient 10 receiving a topical application of an opioid drug, such as morphine sulfate, admixed with a skin penetration enhancer, using a spray 12. In particular, a small quantity of the morphine sulfate solution is then sprayed onto a painful area 14 on a patient 10 to provide the particular pain relief described above.

As a specific example, 90 mg of morphine sulfate and 2700 mg of lecithin may be diluted in 120 cc of saline to form the spray 12. The morphine sulfate/lecithin is initially provided as a solution of 10 mg/cc, whereby the final spray solution contains 90 mg in a total of 129 cc. Thus, the final concentration of morphine in the spray is 0.69 mg/cc. The specific application may result in approximately 2 to 3 mg of morphine in solution to cover approximately a 6×6 square inch area.

FIG. 2 illustrates the same patient 10 with a painful area 14 with an opioid, such as morphine sulfate, admixed with lecithin, and applied topically in either a gel or a cream.

As a specific example, 90 mg of morphine sulfate and 2700 mg of lecithin may be mixed with 120 cc of a topical gel. Again the morphine sulfate/lecithin is initially provided in solution as 10 mg/cc and with the resultant mixture 16 comprising 90 mg of morphine sulfate in a total of 129 cc. The resultant set or cream is applied to the painful area 14 whereby 2 to 3 mg of morphine sulfate covers an area of approximately 6×6 square inches.

DETAILED DESCRIPTION OF THE INVENTION

Prior to the work disclosed in U.S. Pat. No. 5,589,480, there was a body of studies determining that opioid receptors were found in various peripheral tissues and that peripheral opioid effects would be more pronounced in inflamed than in non-inflamed tissues; however, there was no specific determination of how to provide an analgesic effect, using narcotics such as morphine, other than by injection of morphine into a closed space such as a joint. U.S. Pat. No. 5,589,480 disclosed a method and preparation for a topical application of an opioid drug, such as morphine, for a direct activation of the peripheral opioid receptors on the surface of inflamed skin, without any substantial transdermal or transmucosal systemic delivery of the opioid.

The fact that the opioid effects are more pronounced in inflamed than in non-inflamed tissues is a considerable advantage considering that most painful conditions are associated with inflammation, for example, cancer, arthritis, trauma, post-operative pain, skin lesions, etc. The work disclosed in U.S. Pat. No. 5,589,480 demonstrated that extremely small systemically inactive doses of both conventional opioid drugs such as morphine, as well as other opioid agents, can produce potent analgesic effects after local application to inflamed skin in peripheral tissue.

Initially, it was thought that it would be necessary to inject the morphine into an inflamed area since the inflammation activates the opioid receptors and it was also believed that the morphine had to be in an enclosed space to stay in contact with the area that was inflamed. The initial experiments were conducted in conjunction with arthroscopic surgery of the knee and a number of patients were medicated after arthroscopic surgery with injected morphine. These patients were medicated either with morphine alone, with a local anesthetic such as Marcaine or a combination of Marcaine and 1 mg of morphine. It was shown that patients receiving morphine into the joint had significantly more pain relief than patients receiving the same dose intravenously (demonstrating a local effect) and that this effect was mediated by intraarticular opioid receptors. Furthermore, patients who received just Marcaine after the surgery had relief but the relief typically did not extend beyond 12 hours or at most the next day after surgery. The patients who received Marcaine plus one mg of morphine in the knee had much better relief extending for at least twice as long as those that received Marcaine alone.

At this point, it was still thought that it was necessary to keep the morphine in a closed space, such as in a knee, and the results of such controlled clinical studies reporting analgesia produced by morphine injected into the knee joint were reported in Stein et al., N. Engl. J. Med., 325:1123–1126 (1991); Comment in N. Engl. J. Med., 325:1168–1169 (1991) and Khoury et al., Anesthes. 77:263–266 (1992). These studies have been replicated by several other groups throughout the world, but this application of morphine was relatively restricted to the practice of orthopedic surgeons using the morphine injected into a joint after arthroscopic surgery and further progress was restricted because it was thought that the morphine had to be contained in the closed space so as to keep the medication in close contact with the inflamed area.

Nevertheless, in the clinical practices of the inventors of U.S. Pat. No. 5,589,480, while the need for adequate treatment and relief of pain in inflamed skin was evident, there was a lack of evidence that human skin contained peripheral opioid receptors, and there was doubt whether topical administration in the absence of the enclosed conditions akin to administration into the intra-articular space would work. Thus, the inventors of U.S. Pat. No. 5,589,480 conceived and developed a method of carrying out the concept of effecting topical local analgesia in inflamed skin with opioid agents.

Without wishing to be bound by theory, it is believed that the inflammatory process in peripheral tissue is associated with an increase in sensitivity to the antinociceptive effects of opioid agents, perhaps by activation of opioid receptors located on primary afferent neurons. This may occur by one or more means, e.g., de novo synthesis of opioid receptors which increases the number of receptors; axonal transport of pre-existing receptors to peripheral nerve terminals increasing their concentration and thus sensitivity; some other means of activation of pre-existing neuronal opioid receptors by the inflammatory process. See, e.g., Stein, C., Peripheral and non-neuronal opioid effects. Curr. Opin. Anaesth. 7:347–351 (1994). In addition, again without wishing to be bound by theory, inflamed skin is generally more permeable to topically-administered agents, because the inflammatory process destroys Schwann cells in the epidermis, leading to further exposure of the nerve terminals; inflammation also causes edema, which results in loss of integrity of the epidermis, making the nerve terminals more accessible to topical agents.

Thus, although the work described in U.S. Pat. No. 5,589,480 demonstrated the effectiveness of topically-applied opioid analgesics without systemic delivery in inflamed skin, the treatment of peripheral pain in the case of non-inflamed skin faced the additional hurdles of lesser skin permeability, which thus required the addition of skin penetration enhancers and thus risked unwanted systemic delivery, and also did not have the same basis for expecting a successful outcome, i.e., that the inflammatory process in peripheral tissue is associated with an increase in sensitivity to the antinociceptive effects of opioid agents, e.g., due to an increase in the number and/or sensitivity of opioid receptors at peripheral nerve terminals induced by the inflammatory process. Therefore, it could not be predicted whether or how topical analgesia could be induced in non-inflamed skin or mucosa, at least without effecting systemic transdermal or transmucosal delivery as well.

Moreover, it was desired to improve, if possible, the effectiveness of topical opioid analgesia induced in inflamed skin or mucosal tissue, without effecting systemic delivery of the opioid agents.

As expected, application of the pharmaceutical preparations in accordance with those disclosed in U.S. Pat. No. 5,589,480, which comprised, e.g., morphine sulfate in a simple pharmaceutically acceptable topical excipient, e.g., water, saline or hydrophilic gel such as KY Jelly, when applied to intact, non-inflamed skin in a patient suffering from non-inflammatory skin pain such as peripheral neuropathy, did not work. However, when skin-specific penetration enhancers are added to the topical formulation, it was found that even pain arising in non-inflamed skin could be successfully treated with topical, local opioid agents in the absence of delivery of clinically effective systemic opioid levels. Moreover, these skin penetration enhancers were surprisingly shown to improve the effectiveness of local opioid agents in the treatment of pain in inflamed skin or mucosal tissue without the concomitant delivery of substantial amounts of the opioid agent into the systemic circulation.

By "a skin-specific penetration enhancer" is meant an agent which enhances the penetration of an opioid analgesic agent through the uppermost layers of non-inflamed skin to the skin layers in which the peripheral nerves are located that are involved in the painful condition, e.g., diabetic peripheral neuropathy or post-herpetic neuralgia, without further transmission or delivery to the systemic circulation. In some cases, the skin-specificity of the penetration enhancer will be determined by its concentration; e.g., at a concentration of 22%, lecithin has been shown to be an excellent vehicle for enhancing transdermal delivery to the systemic circulation, whereas it has been shown herein that at a concentration of 3–6% in non-inflamed skin, lecithin potentiates the passage of morphine sulfate across the epidermis into the dermis, yet very little, if any, of the active agent is carried beyond those two layers into the bloodstream. Similarly, at concentrations of 3–6%, lecithin can enhance transport of morphine sulfate across the epidermis and into the dermis in inflamed skin, without further transport of substantial amounts into the systemic circulation.

The invention has been tested on a number of patients, and the results are set forth in the Examples. In particular, patients for whom various types of non-in-flamed skin conditions, both acute and chronic, were causing intense pain which was not sufficiently alleviated by systemic administration of opioids were treated topically with various formulations of morphine sulfate and skin penetration enhancers. Patients suffering from intense pain from inflamed skin conditions got more relief from preparations containing enhancers than from preparations lacking them.

The results were accomplished with the use of only two or three mg of the opioid drug, such as morphine, diluted to be sprayed or applied to a relatively large area of skin such as six inches square and without any side effects such as addiction, dullness in the brain, respiratory depression, nausea, vomiting or itching. All of this was accomplished without any significant absorption of the morphine into the blood stream, since the morphine was merely applied topically to the skin or mucous membranes with a transdermal or transmucosal penetration enhancing agent effective only to transmit the morphine into, rather than through, the skin or mucosa.

In addition to the topical application of the opioid, e.g., morphine, using a spray, the opioid may be applied using a variety of different topical formulations such as gels, creams, etc. Depending upon the particular type of non-inflammatory skin lesion, the topical application will reduce pain in lesions such as diabetic neuralgia and post-herpetic neuralgia, e.g., after herpes zoster (shingles) flare-ups. Other types of pain treatable by the methods and compositions disclosed herein include pain associated with damage to peripheral nerves resulting from chemotherapy treatment for a variety of diseases, including cancer and AIDS. For example, Vincristine chemotherapy can result in peripheral neuropathy not associated with an inflammatory process. The main advantage of the method and pharmaceutical preparations disclosed herein is the excellent pain relief without the typical side effects associated with systemically-effective amounts of oral or injectable narcotics which function in the central nervous system. The potential for the present invention is widespread and the topical application opens up a whole new use of narcotics without the prior associated problems.

In both methods of application as shown in FIGS. 1 and 2 the relief is substantial and with continued application on a periodic basis to continue this relief without any of the typical side effects such as addiction, nausea, inhibition of breathing, somnolence and dysphoria which would typically result if morphine were received by the brain. The quantities of the applied opioid described above are illustrative only and it is to be appreciated that lesser and greater quantities may be used, which can be routinely optimized by the skilled worker. In general, amounts analgesically equivalent to 1–3 mg morphine sulfate applied to an area of 6 in$^2$, or 0.0012–0.0042 mg/kg of body weight, are preferred. However, any quantity of opioid used in the topical application of the present invention is a small fraction of the typical dosage used in other methods of opioid treatment.

Analgesic Agents: It is to be appreciated that all the present invention has been described primarily with reference to the use of morphine in the form of morphine sulfate. Other opioid analgesic drugs and other forms of morphine may be used to interact with the peripheral opioid receptors which are present in inflamed peripheral tissues in various areas of the body and the invention is not to be limited specifically to morphine or morphine sulfate.

Suitable opioid analgesic agents include compounds which have an analgesic effect through binding to any opioid receptor, e.g., a mu-, delta- or kappa-receptor, whereby antinociceptive properties of the agent are functional at the site of pain. Examples of such opioid analgesic agents include, but are not limited to morphine, cyclazocine, piperidine, piperazine, pyrrolidine, morphiceptin, meperidine, trifluadom, benzeneacetamine, diacylacetamide, benzomorphan, alkaloids, peptides, phenantrene and pharmaceutically acceptable salts, prodrugs or derivatives thereof. Specific examples of compounds contemplated by as suitable in the present invention include, but are not limited to morphine, heroin, hydromorphone, oxymorphone, levophanol, methadone, meperidine, fentanyl, codeine, hydrocodone, oxycodone, propoxyphene, buprenorphine, butorphanol, pentazocine and nalbuphine. As used herein, "pharmaceutically acceptable salts, prodrugs and derivatives" refers to derivatives of the opioid analgesic compounds that are modified by, e.g., making acid or base salts thereof, or by modifying functional groups present on the compounds in such a way that the modifications are cleaved, either in routine manipulation or in vivo, to produce the analgesically active parent compound. Examples include but are not limited to mineral or organic salts of acidic residues such as amines, alkali or organic salts of acidic residues such as carboxylic acids, acetate, formate, sulfate, tartrate and benzoate derivatives, etc. Suitable opioid analgesic agents, including those specifically mentioned above, are also described in Goodman and Gilman: Pharmaceutical Basis of Therapeutics. 9th Edition, McGraw Hill 1995, chapter 28, pp. 521–555.

In addition, of course, other active agents may be included in the pharmaceutical composition as required, e.g., topically-effective anaesthetics such as xylocaine, cocaine, lidocaine, benzocaine, etc., which may provide a more immediate, if less effective in the long run, level of pain relief until the opioid agent becomes fully effective. Other active agents which may be present in the pharmaceutical preparations include, e.g., antibiotics, and especially those agents which themselves cause pain when applied to the inflamed site due to their inherent properties such as pH.

Additional agents can also be administered, preferably topically, to potentiate the effects of the topically-administered analgesic agents. For example, dextromethorphan, a non-addictive opioid compound, can be co-administered, preferably topically, although parenteral administration is also effective, to enhance the effectiveness of the topically administered analgesic agent. Without wishing to be bound by theory, it is believed that dextromethorphan has previously unappreciated analgesic properties in peripheral nerves. Suitable concentrations of dextromethorphan are routinely ascertainable by the skilled worker, and include the normal therapeutic amounts administered parenterally for conventional purposes, e.g., as a cough suppressant, or less, and routinely determinable amounts for topical administration; for example, 1 g of dextromethorphan can be added to a composition of Example 1 to provide additional relief from pain.

Transdermal Enhancers: The most important criterion for selecting a suitable topical excipient is that, while it enhances percutaneous delivery of the opioid analgesic agent into the skin or mucous membrane, it does not enhance delivery of the analgesic agent through the skin or mucosa into the systemic circulation, e.g., it does not provide substantial transdermal or transmucosal transmission. In the case of some enhancers, the amount and rate of transmission and thus the difference between providing transdermal or transmucosal delivery and not doing so will lie in the selection of the amount of enhancer used, the intactness of the skin, the type of skin or mucosal tissue which is being treated, the nature of the opioid agent, etc. However, these are routinely determinable parameters which can be optimized for a particular condition by one of ordinary skill in the art.

Various methods have been used to increase skin permeation of drugs include penetration enhancers, prodrugs, superfluous vehicles, iontophorosis, phonophoresis and thermophoresis. In particular, penetration enhancers are preferred.

Ideal penetration enhancers have no irritancy or toxicity to the skin, as well as high enhancing effects. Enhancers themselves should be physiochemically stable and not have pharmacologic effects and preferably should not have smell, color or taste.

The stratum corneum provides the principal barrier to the percutaneous penetration of topically applied substances. It is the most superficial, cutaneous layer, the horny layer, which consists of flat, scalelike "squames" made up of the fibrous protein keratin. The squames are continually being replaced from below by epidermal cells that die in the process of manufacturing keratin. It is unlikely that the emulsified fat on the skin surface greatly affects permeability. However, vehicles can control, to a great extent, the rate of penetration of drugs that are applied to the skin. The intercellular lipids may be important for the permeability barrier in skin.

It is known that some combinations of enhancers are synergistic in action, as with ethanol as a vehicle for the potent enhancer laurocapram. Some combinations are not synergistic; for instance, (N) decylmethylsulfoxide lowers the zeta potential of the skin; thus, enhancement due to conduction flow (iontophoresis) is minimized. In any case, optimization of suitable transdermal or transmucosal enhancing preparations for a given use is routine for one of ordinary skill in the art.

Thus, suitable topical transdermal or transmucosal enhancing agents can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87. For example, suitable enhancers for transdermal absorption include ethanol, propylene glycol, water, sodium oleate, leucinic acid, oleic acid, capric acid, sodium caprate, lauric acid, sodium laurate, neodecanoic acid, dodecyl-amine, cetryl lactate, myristyl lactate, lauryl lactate, methyl laurate, phenyl ethanol, hexamethylene lauramide, urea and derivatives, dodecyl N, N-dimethylamino acetate, hydroxyethyl lactamide, phyophatidylcholine, sefsol-318 (a medium chain glyceride), isopropyl myristate, isopropyl palmitate, several surfactants, including polyoxyethylene (10) lauryl ether (Brij 361 R), diethyleneglycol lauryl ether (PEG-2-L), laurocapram (Azone; 1,1-dodecylazacycloheptan-2-one), acetonitrile, 1-decanol, 2-pyrrolidone, N-methylpyrrolidone, N-ethyl-1-pyrrolidone, 1-Methyl-2-pyrrolidone, 1-lauryl-2-pyrrolidone, sucrose monooleate, dimethylsulfoxide (DMSO) about 80% concentration required, decylmethylsulfoxide (n) enhances primarily polar or ionic molecules (soluble in ethanol), acetone, polyethylene glycol 100–400 MW, dimethylacetamide, dimethylforamide, dimethylisosorbide, sodium bicarbonate, various $N_{7-16}$-alkanes, mentane, menthone, menthol, terpinene, D-terpinene, dipentene, N-nonalol and limonene.

Without wishing to be bound by theory, the following outline sets forth proposed mechanisms of action of common chemical penetration enhancers:

Sulfoxides (e.g., dimethyl sulfoxide [DMSO], N-decylmethylsulfoxide)

Reduces resistance of the skin to the drug molecule

Promotion of drug partitioning from the dosage form

Elution of lipid, lipoprotein and nucleoprotein structures of the stratum corneum Increase lipid fluidity by disrupting tightly packed lipid chains which results in an interaction between polar head groups of the lipids via hydrogen bonding Protein interactions resulting in a change in protein conformation, thus creating a passage of aqueous channels May increase polar drugs more effectively than nonpolar drugs Alcohols (e.g., ethanol)

Increase solubility of drug in fatty matrix of stratum corneum

Extraction of lipidic and peptidic substances, therefore creating a porous pathway for polar compounds Polyols (e.g., propylene glycol)

Solubilize alpha-keratin and occupy hydrogen bonding sites, thus reducing drug-tissue bonding sites and promoting permeation Fatty Acids (e.g., lauric, myristic, palmitic, stearic)

Disrupt membrane lipid packing by selective perturbation of the intercellular lipid bilayers present in the stratum corneum Esters (e.g., isopropyl palmitate, isopropyl myristate)

Increase lipid fluidity by forming a solvation shell around polar head groups which leads to a disruption of lipid packing Permeation into liposomal bilayers, thus increasing fluidity and promoting permeation of drug molecules Increasing diffusivity of the stratum corneum and the partition coefficient between the stratem corneum and vehicle of both drug and solvent Amides (e.g, urea)

Increase moisture of the skin

Act as a mild keratolytic through an ability to split hydrogen bonds between cells in the stratum corneum Surface-Active Agents (e.g., Pluronic F127, sodium lauryl sulfate, lecithin, docusate sodium, polysorbates)

Absorb at interfaces and interact with biological membrane

Removal of water-soluble agents that normally act as plasticizers

Emulsify sebum, thereby enhancing the thermodynamic activity coefficients of drugs Extraction of lipids from the stratum corneum Penetration of surfactant into the intercellular lipid matrix of the cornified layer Water (occlusion)

Cause swelling of the corneocytes

Increase the amount of water associated with the intercellular lipid domain

Increase the temperature

Increase lipid fluidity and disorder

May induce lipid phase separation by altering the equilibrium interaction between water and intercellular lipid domains Prevent evaporation of transpirational moisture Topical Excipients: The choice of topical excipient as a vehicle for the analgesic agent, while routine, is an important aspect of the claimed invention. The most important criterion for selecting a suitable topical excipient is that it does not enhance delivery of the analgesic agent to the systemic circulation, e.g., substantial transdermal or transmucosal transmission. For example, in general, it is preferred that the topical excipient not have substantial occlusive properties, which enhance percutaneous transmission of the opioid analgesic agent through the skin or mucosa into the systemic circulation. Such occlusive vehicles include hydrocarbon bases such as white petrolatum (e.g., Vaseline); anhydrous absorption bases such as hydrophilic petrolatum and anhydrous lanolin (e.g., Aquaphor); and water-in-oil emulsion bases such as lanolin and cold cream.

More preferred are vehicles which are substantially nonocclusive, and generally include those which are water-soluble, such as oil-in-water emulsion bases (creams or hydrophilic ointments) and water-soluble bases such as polyethylene glycol-based vehicles and aqueous solutions gelled with various agents such as methylcellulose, hydroxyethyl cellulose, and hydroxypropyl methylcellulose (e.g., K-Y Jelly).

Suitable topical excipients and vehicles can be routinely selected for a particular use by those skilled in the art, and especially with reference to one of many standard texts in the art, such as Remington's Pharmaceutical Sciences, Vol. 18, Mack Publishing Co., Easton, Pa. (1990), in particular Chapter 87.

Other additives, e.g., for enhancing the adherent properties of the pharmaceutical preparation to various special skin areas, e.g., the axillar, plantar and palmar skin, and mucosal tissues, e.g., in the mouth, on the throat, on the genitalia, particularly the external female genitalia, can be similarly routinely selected and the preparation adapted to such use by one of ordinary skill in the art.

Other Definitions: By "mucosal tissue" is meant tissue comprising a superficial epithelial membrane which is lubricated by mucus. This includes, inter alia, the lining of the mouth, throat, nose, tympanic membrane, external female genitalia, vagina, urethra, rectum and anus. It does not include the conjunctiva of the eye.

By "directly activate peripheral opioid receptors in the skin or mucosal tissue, but not sufficient to activate central nervous system opioid receptors" is meant that the analgesic action of the opioid is mediated through interaction with the peripheral opioid receptor, e.g., and not through interaction with CNS receptors. See, e.g., Stein (1993), supra, which sets forth criteria for evaluating peripheral opioid receptor antinociception.

By "substantial absence of" or "does not enhance" transdermal or transmucosal delivery of the opioid analgesic agent is meant that upon the induction of analgesia, less than 25%, preferably less than 10%, more preferably less than 5%, still more preferably 1% and most preferably none of the opioid analgesic agent has passed through the stratum corneum into the systemic circulation. In particular, an insufficient amount for induction of systemic analgesia is delivered to the systemic ciruclation.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the foregoing and in the following examples, all temperatures are set forth uncorrected in degrees Celsius; and, unless otherwise indicated, all parts and percentages are by weight.

The entire disclosures of all applications, patents and publications, cited above and below, including U.S. Ser. No. 08/291,614, filed Aug. 17, 1994, now U.S. Pat No. 5,589,480, and U.S. Ser. No. PCT/96/19618, filed Dec. 12, 1996, are hereby incorporated by reference.

EXAMPLES

Example 1: Peripheral Neuropathy in the Feet

The patient has severe peripheral neuropathy on both feet, uncontrolled with oral narcotics or other medications. The patient was treated with nerve blocks which provided him with relief only for a few hours and then the pain comes back. He describes burning which is debilitating and he is unable to stand on his feet because of the pain. A topical application of morphine in KY gel afforded no relief. The patient was then given topical morphine with lecithin to control the pain and the patient had excellent results with it. The patient used the formulation three times a day as a mixture of 120 mg of morphine and 120 cc of a base including phospholipids (4% lecithin). The patient was very amenable to treatment, as it was providing him with excellent relief and he had no side effects.

Example 2: Peripheral Neuropathy in the Feet Resulting From Vincristine Chemotherapy The patient is a 57-year-old gentleman with peripheral neuropathy due to the use of Vincristine for the treatment of Hodgkin's Disease. The patient had severe peripheral neuropathy on his feet and is unresponsive to multiple oral medications without any relief and the burning was very debilitating. The patient was offered topical narcotics, 120 mg of morphine in 120 cc of a base containing lecithin phospholipid and the patient applied it twice. He would take it to his office with him to work as he would use it in the morning and take it at noon and use it in the evening. The patient had excellent relief with no side effects.

Example 3: Diabetic Neuropathy in the Hands

The patient is a 58-year-old female with diabetic neuropathy in the hands, mainly on the right. The patient had severe pain, uncontrolled with any kind of treatment including oral medications. The patient was offered topical hydrocodone with lecithin and felt relief within 15 minutes of application. The relief lasted for many hours. The patient had no side effects.

Example 4: Severe Peripheral Neuropathy of the Feet

The patient is a 61-year-old male with severe peripheral neuropathy in his feet The patient was a mechanic for a period of time at his job. The pain was unrelieved with any treatment and the patient was then tried on topical morphine with 120 mg of morphine and 120 cc of a base containing lecithin phospholipid with excellent relief of pain. The patient used it three times a day and had very good control of his pain without any side effects.

Example 5: Crippling Diabetic Peripheral Neuropathy in the Feet

The patient is a 57-year-old gentleman with a diabetic peripheral neuropathy, complaining of severe burning pain of his feet. The patient was unable to walk due to the severity of his pain. He was desperate, as oral narcotics were not helping him. The patient was first treated with topical morphine in KY gel, without relief. The patient was then administered 120 mg of morphine in 120 cc of a base containing phospholipid (2700 mg of lecithin). The patient used it every four hours. The patient states that this provided good relief, about 50% relief, and made it reasonable for him to tolerate the remaining pain. He stated that the best results would come at night as this would allow him go to go sleep because the pain would be tolerable. He had no side effects pertaining to the morphine.

Example 6: Peripheral Neuropathy in the Feet

A 68-year-old gentleman with peripheral neuropathy with severe pain in his feet, who was unresponsive to oral medication or nerve blocks. The patient was first treated with topical morphine in KY gel, without relief. The patient was then offered the use of topical morphine 120 mg in 120 cc of base of phospholipid and the patient had good relief of his pain, in the range of 57%, without any side effects. The patient did have relief for three to five hours and it helped him sleep at night, as it abated the pain and the sensitivity in his feet. The patient did not report any side effects.

Example 7: Composition

An exemplary composition according to the invention comprises:

| | |
|---|---|
| Morphine: | 120 mg |
| Polyethylene glycol: | to wet |
| Soya lecithin: | 2700 mg (4.5 ml) |
| White petrolatum: | 84 g |
| Dextromethorphan: | 1 g |
| Pluronic 30% | 30 ml |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A topical pharmaceutical composition comprising an admixture of an opioid analgesic agent, a skin- or mucosal-specific penetration enhancer and a pharmaceutically acceptable excipient for topical administration to inflamed or non-inflamed skin or mucosal tissue, wherein a unit dosage amount of the admixture contains a systemically ineffective amount of the opioid analgesic agent, and the amount of penetration enhancer is effective to enhance penetration of the opioid agent into the skin or mucosal tissue, and the penetration enhancer and excipient do not enhance transdermal or transmucosal transmission of the opioid analgesic agent to the systemic circulation, with the proviso that, when the admixture is a liquid, it further comprises a component that is pharmaceutically unacceptable for parenteral administration, wherein the opioid analgesic agent is morphine, cyclazocine, piperidine, piperazine, pyrrolidine, morphiceptin, trifluadom, benzeneacetamine, diacylacetamide, benzomorphan, heroin, hydromorphone, levophanol, methadone, meperidine, fentanyl, codeine, hydrocodone, oxycodone, propoxyphene, buprenorphine, butorphanol, pentazocine or nalbuphine, and wherein a unit dosage amount of the opioid analgesic agent is analgesically equivalent to up to 3 mg of morphine per 6 $in^2$ of skin.

2. A topical pharmaceutical composition of claim 1, wherein the opioid analgesic agent is morphine or morphine sulfate.

3. A topical pharmaceutical composition of claim 1, wherein the excipient is a liquid and the admixture is administered by spraying the liquid onto the skin or mucosal tissue.

4. A topical pharmaceutical composition of claim 1, wherein the excipient is a gel or cream and the admixture is administered by spreading the gel or cream on the skin or mucosal tissue.

5. A topical pharmaceutical composition of claim 1, in a unit dosage form analgesically equivalent to 2–3 mg of morphine.

6. A topical pharmaceutical composition of claim 1, wherein the skin- or mucosal-specific penetration enhancer is lecithin.

* * * * *